United States Patent
Smith et al.

(10) Patent No.: US 9,936,958 B2
(45) Date of Patent: Apr. 10, 2018

(54) ZIP CLIP

(71) Applicant: Boston Scientific Scimed, Inc., Maple Grove, MN (US)

(72) Inventors: Paul Smith, Smithfield, RI (US); Michelle Fater, Worcester, MA (US); Shawn Kerr, Lancaster, MA (US); Priya Khanchandani, Marlborough, MA (US); Dylan Murphy, Walpole, MA (US); Kevin Wilcox, Brighton, MA (US); Daniel R. Quinn, Littleton, MA (US); Michael E. Zupkofska, Rockland, MA (US); Kenny J. King, Gainesville, FL (US); Rachael A. Rheaume, Framingham, MA (US); Kerry L. Grant, Northbridge, MA (US); John A. Hingston, Framingham, MA (US); Brian Gaffney, Rutland, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 243 days.

(21) Appl. No.: 14/706,761

(22) Filed: May 7, 2015

(65) Prior Publication Data

US 2015/0327863 A1    Nov. 19, 2015

Related U.S. Application Data

(60) Provisional application No. 61/994,523, filed on May 16, 2014.

(51) Int. Cl.
*A61B 17/12* (2006.01)
*A61B 17/128* (2006.01)
(Continued)

(52) U.S. Cl.
CPC ...... *A61B 17/1285* (2013.01); *A61B 17/0057* (2013.01); *A61B 17/068* (2013.01);
(Continued)

(58) Field of Classification Search
CPC .............. A61B 17/083; A61B 17/1227; A61B 17/0644; A61B 17/068; A61B 2017/0641; A61B 2017/0645; A61B 2017/081
See application file for complete search history.

(56) References Cited

U.S. PATENT DOCUMENTS

| 4,467,805 A | * | 8/1984 | Fukuda | A61B 17/0644 606/217 |
| 4,671,278 A | * | 6/1987 | Chin | A61B 17/083 606/143 |

(Continued)

*Primary Examiner* — Alexander Orkin
(74) *Attorney, Agent, or Firm* — Fay Kaplun & Marcin, LLP

(57) ABSTRACT

A tissue closure device includes a first clip including a first longitudinal element extending along a longitudinal axis from a proximal end to a distal end and a first pair of arms extending laterally from the first longitudinal element, the first pair of arms movable between an open configuration in which free ends of the first pair of arms are separated from one another and a closed configuration in which the free ends of the first pair of arms extend toward one another, the first pair of arms being biased toward the closed configuration, and a sliding element extending from a proximal end to a distal end and longitudinally movable relative to the first clip so that when a portion of the sliding element is received between the first pair of arms, the first pair of arms is moved from the biased closed configuration to the open configuration.

18 Claims, 7 Drawing Sheets

(51) Int. Cl.
- *A61B 17/08* (2006.01)
- *A61B 17/00* (2006.01)
- *A61B 17/064* (2006.01)
- *A61B 17/068* (2006.01)
- *A61B 17/122* (2006.01)
- *A61B 90/00* (2016.01)

(52) U.S. Cl.
CPC ........ *A61B 17/0644* (2013.01); *A61B 17/083* (2013.01); *A61B 17/1227* (2013.01); *A61B 2017/00566* (2013.01); *A61B 2017/00646* (2013.01); *A61B 2017/00818* (2013.01); *A61B 2017/0641* (2013.01); *A61B 2017/0645* (2013.01); *A61B 2017/081* (2013.01); *A61B 2017/088* (2013.01); *A61B 2090/037* (2016.02)

(56) References Cited

U.S. PATENT DOCUMENTS

| | | | | |
|---|---|---|---|---|
| 4,791,707 A * | 12/1988 | Tucker | ............... | A61B 17/083 227/120 |
| 5,730,746 A * | 3/1998 | Walder-Utz | ......... | A61B 17/128 606/143 |
| 6,322,580 B1 * | 11/2001 | Kanner | ............... | A61B 17/0057 606/213 |
| 8,202,293 B2 * | 6/2012 | Ellingwood | ....... | A61B 17/0057 606/139 |
| 8,403,956 B1 * | 3/2013 | Thompson | ........... | A61B 17/072 227/175.1 |
| 2002/0062130 A1 * | 5/2002 | Jugenheimer | ........ | A61B 17/122 606/142 |
| 2003/0036755 A1 * | 2/2003 | Ginn | ................... | A61B 17/0644 606/41 |
| 2007/0118163 A1 * | 5/2007 | Boudreaux | .......... | A61B 17/064 606/157 |
| 2007/0213747 A1 * | 9/2007 | Monassevitch | .... | A61B 17/0643 606/151 |
| 2009/0242609 A1 * | 10/2009 | Kanner | ............... | A61B 17/0057 227/175.1 |
| 2011/0054521 A1 * | 3/2011 | Ventura | .............. | A61B 17/0057 606/216 |
| 2012/0228355 A1 * | 9/2012 | Combrowski | ..... | A61B 17/0401 227/175.1 |
| 2014/0371766 A1 * | 12/2014 | Morris | ............... | A61B 17/1227 606/143 |

\* cited by examiner

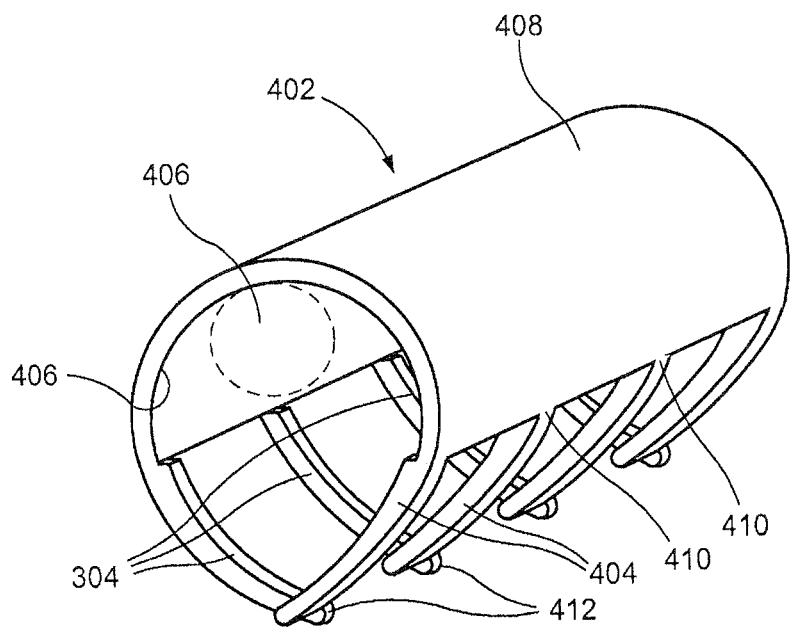
F I G. 12
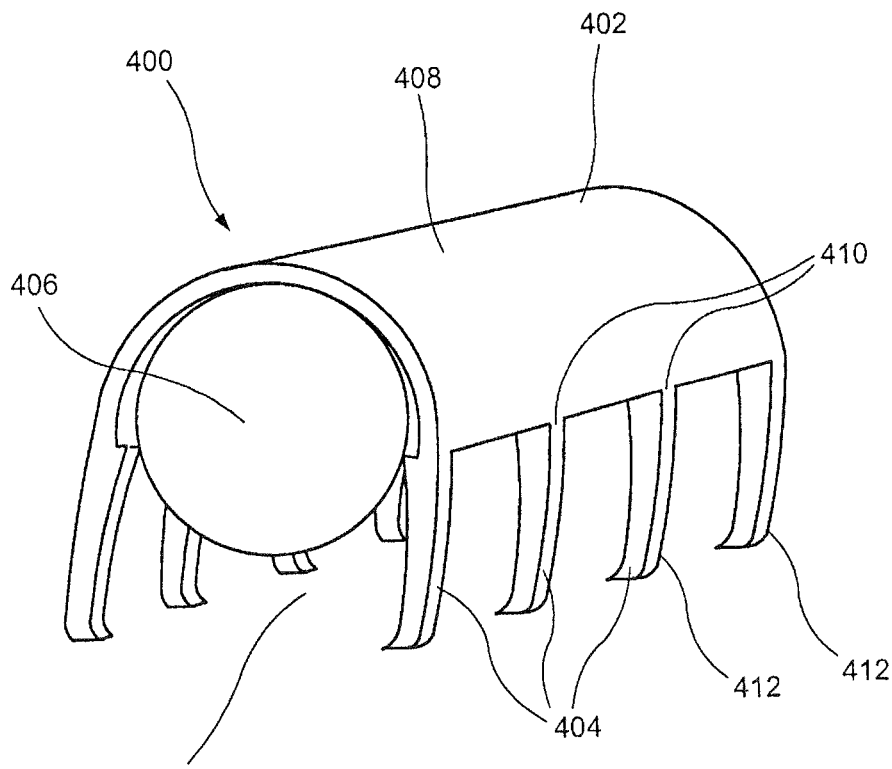
F I G. 13

ZIP CLIP

PRIORITY CLAIM

The present application claims priority to U.S. Provisional Patent Application Ser. No. 61/994,523 field May 16, 2014; the disclosure of which is incorporated herewith by reference.

BACKGROUND

Physicians have become increasingly willing to perform more aggressive interventional and therapeutic endoscopic procedures including, for example, the removal of larger lesions (e.g., cancerous masses), tunneling under the mucosal layer of the gastrointestinal (GI) tract to treat tissues below the mucosa, full thickness removal of tissue, the treatment of other organs by penetrating and passing instruments out of the GI tract, and endoscopic treatment/repair of post-surgical issues (e.g., post-surgical leaks, breakdown of surgical staple lines, anastomotic leaks). These procedures may increase the risk of perforating the wall of the GI tract, or may require closure of the GI tract wall as part of the procedure. Endoscopic closure reduces costs for the hospital and provide benefits to the patient. However, current devices for tissue closure may be difficult to use and/or time consuming. In addition, current devices may be insufficient to close for certain perforations or to treat certain conditions and anatomies such as, for example, large wounds created in the GI tract.

SUMMARY OF THE DISCLOSURE

The present disclosure is directed to a tissue closure device, including a first clip including a first longitudinal element extending along a longitudinal axis from a proximal end to a distal end and a first pair of arms extending laterally from the first longitudinal element, the first pair of arms being movable between an open configuration in which free ends of the first pair of arms are separated from one another to receive a target tissue therebetween and a closed configuration in which the free ends of the first pair of arms extend toward one another to grip the target tissue therebetween, the first pair of arms being biased toward the closed configuration, and a sliding element extending from a proximal end to a distal end and longitudinally movable relative to the first clip so that when a portion of the sliding element is received between the first pair of arms, the first pair of arms is moved from the biased closed configuration to the open configuration.

In another embodiment, the present disclosure is directed to a device, wherein the sliding element is a mandrel including an enlarged distal end and a lumen extending therethrough, a portion of the mandrel extending proximally from the enlarged distal end sized and shaped to be slidably received within a gap formed between the first pair of arms in the closed configuration, the mandrel being longitudinally movable relative to the first clip so that when the enlarged distal end is received between the first pair of arms of the first clip, the first clip is moved from the biased closed configuration to the open configuration.

In another embodiment, the present disclosure is directed to a device, wherein the first pair of arms is formed via a flexible member passed through an opening extending laterally through the first longitudinal element.

In yet another embodiment, the present disclosure is directed to a device, wherein the first clip includes a second pair of arms extending laterally from the first longitudinal element, the second pair of arms movable between an open configuration in which free ends of the second pair of arms are separated from one another to receive a target tissue therebetween and a closed configuration in which the free ends of the second pair of arms extend toward one another to grip the target tissue therebetween, the second pair of arms being biased in the closed configuration and positioned along the first longitudinal element proximally of the first pair of arms.

In a further embodiment, the present disclosure is directed to a device, further comprising a second clip including a second longitudinal element extending along a longitudinal axis from a proximal end to a distal end and a third pair of arms extending laterally from the second longitudinal element, the third pair of arms movable between an open configuration in which free ends of the third pair of arms are separated from one another to receive a target tissue therebetween and a closed configuration in which the free ends of the third pair of arms extend toward one another to grip the target tissue therebetween, the third pair of arms biased in the closed configuration.

In another embodiment, the present disclosure is directed to a device, wherein the second clip includes a fourth pair of arms extending laterally from the second longitudinal element, the fourth pair of arms movable between an open configuration in which free ends of the fourth pair of arms are separated from one another to receive a target tissue therebetween and a closed configuration in which the free ends of the fourth pair of arms extend toward one another to grip the target tissue therebetween, the fourth pair of arms being biased in the closed configuration and positioned along the second longitudinal element proximally of the third pair of arms.

In another embodiment, the present disclosure is directed to a device, wherein the proximal end of the first longitudinal member of the first clip is connected to the distal end of the second longitudinal member of the second clip via a frangible link.

In yet another embodiment, the present disclosure is directed to a device, wherein the mandrel includes a longitudinal slot extending along a length of the enlarged distal end so that, when the enlarged distal end is received between the first pair of arms, the longitudinal slot is aligned with a space between the free ends of the first pair of arms such that the target tissue is receivable therebetween.

In a further embodiment, the present disclosure is directed to a device further comprising a vacuum source coupled to a proximal end of the mandrel to provide a suction force to the enlarged distal end via the lumen.

In another embodiment, the present disclosure is directed to a device, wherein each arm of the first pair of arms extend from a first end connected to the first longitudinal element to a second free end.

In another embodiment, the present disclosure is directed to a device, wherein the sliding element is a planar pin slidably receivable between first ends of the first pair of arms.

In yet another embodiment, the present disclosure is directed to a device, wherein the first pair of arms are integrally formed with the first longitudinal element.

The present disclosure is also directed to a tissue closure device, including a clip including a longitudinal element extending along a longitudinal axis from a proximal end to a distal end and a first pair of arms extending laterally from the longitudinal element, the first pair of arms being movable between an open configuration in which free ends of the first pair of arms are separated from one another to receive a target tissue therebetween and a closed configuration in which the free ends of the first pair of arms extend toward one another to grip the target tissue therebetween, the first pair of arms being biased toward the closed configuration, and an inflatable balloon positioned along an interior surface of the first longitudinal element so that when the inflatable balloon is moved from a deflated state to an inflated state, the inflatable balloon is enlarged causing the first pair of arms to be moved toward the open configuration.

In a further embodiment, the present disclosure is directed to a device, further comprising a second pair of arms extending laterally from the first longitudinal element, the second pair of arms movable between an open configuration in which free ends of the second pair of arms are separated from one another to receive a target tissue therebetween and a closed configuration in which the free ends of the second pair of arms extend toward one another to grip the target tissue therebetween, the second pair of arms being biased in the closed configuration and positioned along the first longitudinal element proximally of the first pair of arms.

In another embodiment, the present disclosure is directed to a device, wherein the first pair of arms are integrally formed with the first longitudinal element.

The present disclosure is also directed to a method for closing a tissue opening, comprising inserting a first clip of a tissue closure device into a first target area within a body, the first clip including a first longitudinal element extending along a longitudinal axis from a proximal end to a distal end and including a first pair of arms extending laterally from the first longitudinal element, moving a mandrel received within a space between the first pair arms longitudinally relative to the first clip so that an enlarged distal end of the mandrel is received between the first pair arms, moving the first pair of arms from a biased closed configuration to an open configuration, drawing a first target tissue between free ends of the first pair of arms in the open configuration, and moving the mandrel proximally relative to the first clip to remove the enlarged distal end from between the first pair of arms so that the first pair of arms revert to the biased closed configuration to grip the first target tissue received therebetween.

BRIEF DESCRIPTION OF THE DRAWINGS

FIG. 12 shows a perspective view of a device according to a fourth exemplary embodiment of the present disclosure, in a first configuration; and FIG. 13 shows a perspective view of the device of FIG. 12, in a second configuration.

DETAILED DESCRIPTION

Figure 1:
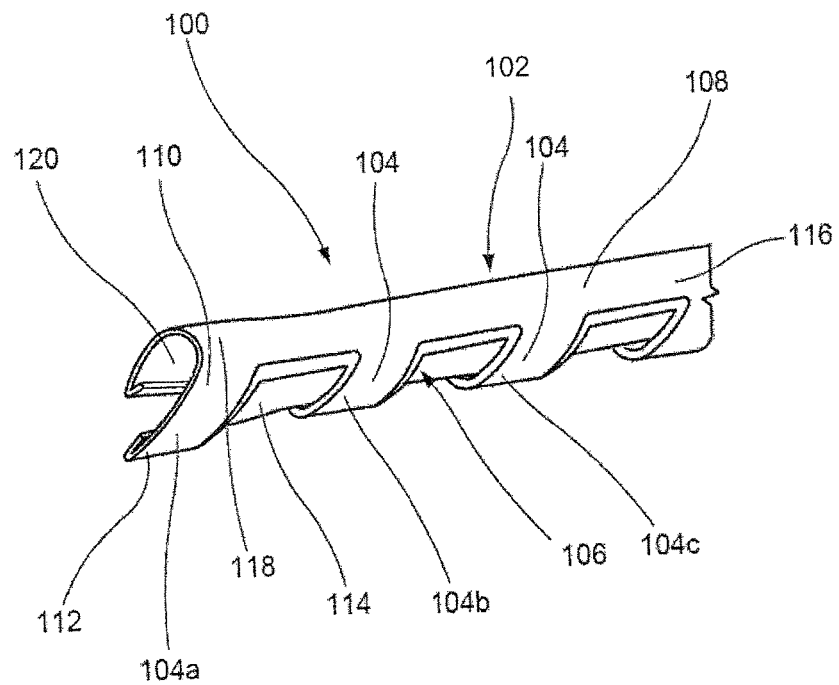
FIG. 1 shows a perspective view of a device according to a first exemplary embodiment of the present disclosure.

The present disclosure may be further understood with reference to the following description and the appended drawings, wherein like elements are referred to with the same reference numerals. Exemplary embodiments of the present disclosure describe endoscopic devices. In particular, exemplary embodiments describe endoscopic clipping devices for tissue closure. A tissue clipping device according to the present disclosure may be passed through the working channel of an endoscope inserted, for example, into GI tract and deployed from a distal end thereof to clip a target tissue. Although exemplary embodiments of the present disclosure specifically describe a device for treating the GI tract, it will be understood by those of skill in the art that devices according to the present disclosure may be used to clip tissue in any of a variety of anatomies for any of a variety of reasons. It should also be noted that the terms "proximal" and "distal" as used herein are intended to refer to a direction toward (proximal) and away from (distal) a user of the device.

As shown in FIGS. 1-5, a tissue closure device 100 according to a first exemplary embodiment comprises a clip 102 including one or more pair of arms 104, and a mandrel 106 for moving the clip arms 104 between an open tissue-receiving configuration and a closed tissue-gripping configuration. The pair of arms 104 extend laterally from a longitudinal element 108 from a first end 110 attached to the longitudinal element 108 to a second free end 112 so that the mandrel 106 is longitudinally movable relative to the longitudinal element 108 of the clip 102 to move the arms 104 between the open and closed configurations. The arms 104 are biased in the closed configuration in which second ends 112 of the arms 104 are drawn toward one another to grip tissue received therebetween. The mandrel 106 extends along a longitudinal axis from a proximal end (not shown) to an enlarged distal end 114 which, when received between the arms 104, moves the arms 104 away from one another to the open configuration with the second ends 112 separated from one another to receive tissue therebetween. The device 100 may further comprise a handle connected to the proximal end of the mandrel 106 and a proximal end of a control member (not shown), a distal end of which is connected to a proximal end of the clip 102, such that when the device 100 is inserted into target area within a body via, for example, an endoscope, the handle extends proximally therefrom to remain accessible to a user of the device 100. The handle includes an actuator for moving the mandrel 106 and the clip 102 relative to one another to separately move arms 104 of each one of the clips 102 between the open and closed configurations. Portions of the device 100 such as, for example, the control member and proximal portions of the mandrel 106 are formed of materials having sufficient flexibility so that the clip 102 and the mandrel 106 may be passed through a body lumen along a tortuous path. Although the exemplary embodiments describe the clip 102 as being inserted into the body via a working channel of an endoscope, it will be understood by those of skill in the art that the clip 102 may be similarly passed through another device such as, for example, a guide tube or a trocar port, etc.

Figure 3:
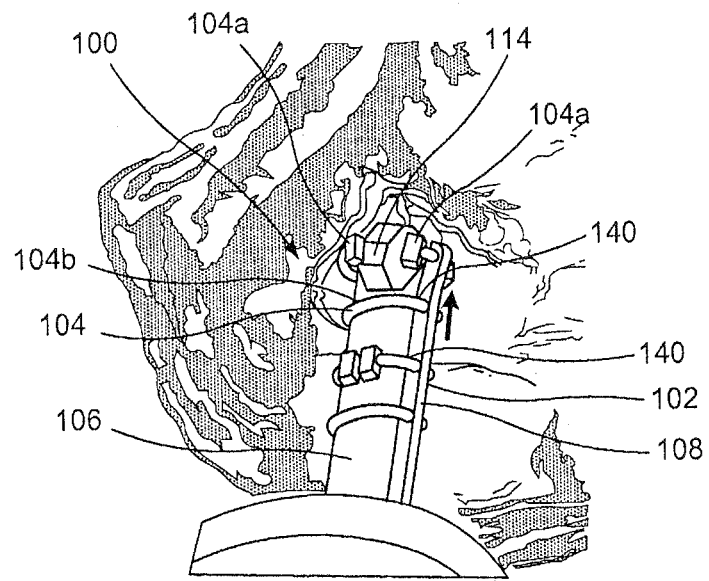
FIG. 3 shows a perspective view of the device of FIG. 1, in an insertion configuration.
Figure 4:
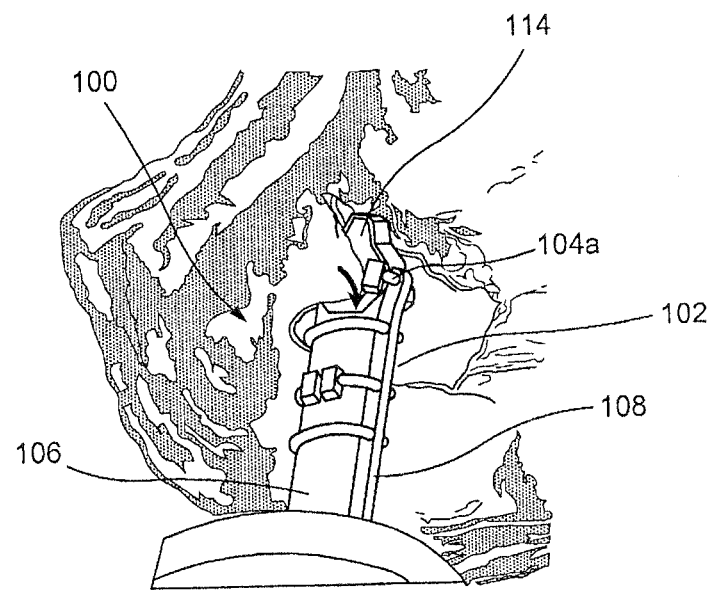
FIG. 4 shows a perspective view of the device of FIG. 1, wherein tissue is being drawn between arms of a first clip thereof.
Figure 5:
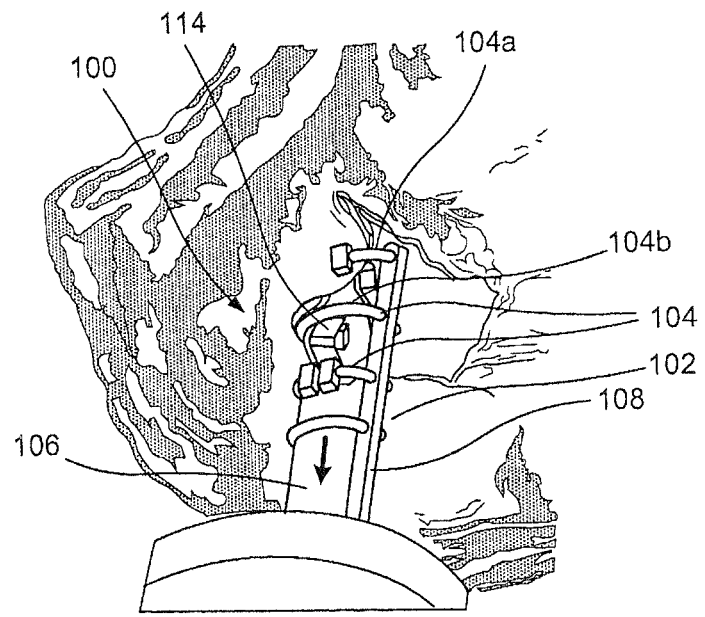
FIG. 5 shows a perspective view of the device of FIG. 1, wherein the first clip is closed over the tissue.

As described above, the clip 102 includes one or more pairs of arms 104 coupled to a longitudinal element 108. The longitudinal element 108 extends along a longitudinal axis from a proximal end 116 to a distal end 118. The arms 104 are arranged in pairs with each pair of arms 104 extending in opposite directions from the longitudinal element 108 at substantially the same point along the longitudinal axis such that the arms 104 of each pair oppose one another. Thus, moving the arms 104 of any of the pairs toward one another to the closed configuration grips tissue between the second ends 112 thereof. As shown in FIG. 1, first ends 110 of the arms 104 are connected to the longitudinal element 108 or, alternatively, may be integrally formed therewith. In another embodiment, as shown in FIGS. 3-5, each of the pair of arms 104 may be formed of a single element such as, for example, a suture or flexible wire, passed through an opening 140 extending laterally through the longitudinal member 108. The suture or flexible wire may be movable within the opening 104 to vary a length of the opposing arms 104 of each pair. Each of the pair of arms 104 may be formed of, for example, spring-tempered stainless steel biased toward the closed configuration and may be overmolded with a plastic such as PP, PC, ABS, PE and/or nylon to provide clamping pads at the second ends 112. Furthermore, the overmolded plastic may form the longitudinal element 108. It will be understood by those of skill in the art, however, that the clip 102 may be formed of any of a variety of materials so long as the clip arms 104 are sufficiently flexible to move between the open and closed configurations while providing a resistive force to the gripped tissue.

A length of the longitudinal element 108 corresponds to a number of pairs of clip arms 104 included in the clip 102. Where the clip 102 includes more than one pair of clip arms 104, adjacent pairs of arms 104 are separated from one another along the length of the longitudinal element 108. For example, a first pair of clip arms 104a may be positioned at the distal end 118 of the longitudinal element 108. The second one of the pairs of clip arms 104b is spaced proximally from the first pair of clip arms 104a along the longitudinal element 108, a distance from the first pair of clip arms 104a. Each subsequent pair of clip arms 104 may be spaced proximally from the immediately distal pair of clip arms 104 along the longitudinal element 108. Where the device 100 includes multiple clip arms 104, each pair of clip arms 104 may be equidistantly spaced from one another along the longitudinal element 108 or separated by any distances chosen to suit the apparatus to a particular procedure.

It will be understood by those of skill in the art that the clip 102 may include any number of pairs of clip arms 104. The number of pairs of clip arms 104 may be selected, for example, depending on a size of an opening to be closed. In one exemplary embodiment, the clip 102 includes a single pair of arms 104 to provide a simple hemostasis clip in which the arms 104 are on opposite sides of a tissue opening. In another embodiment, the clip 102 may include two pair of arms 104a, 104b to approximate opposing edges of a tissue opening at two spots separated along the length of the longitudinal element 108. The first pair of arms 104a may, for example, be clipped over a portion of tissue on a first side of a tissue opening. The longitudinal element 108 may then be moved toward a second side of the tissue opening opposing the first side to draw the first and second sides of the tissue opening together to seal the opening and the second pair of arms 104a, 104b may then be clipped over a portion of tissue on the second side of the tissue opening to maintain the seal on the tissue opening. In another embodiment, the clip 102 may include more than two pairs of arms 104 so that a first of the arms 104a of each pair of arms 104 may be applied to tissue on a first side of the tissue opening while the second arms 104b of each pair of arms 104 is applied to tissue on the second side of the tissue opening to draw the tissue opening closed along its length. Alternatively, a first pair of arms may be applied to grip tissue on the first side of the opening while a second pair of arms 104 adjacent to the first pair of arms 104 grips tissue on the second side of the tissue opening with a third pair of arms 104 gripping tissue on the first side of the tissue opening to close the tissue opening in a zipper-like fashion. Each pair of arms 104 is applied to a portion of tissue on a side of the tissue opening opposite that of adjacent pairs of arms 104 until all of the pairs of arms 104 have been applied over a length of the tissue opening to close the opening.

For example, the first pair of arms 104a is applied to a portion of tissue along the first side of the tissue opening, the second pair of arms 104b is applied to a portion of tissue along the second side of the tissue opening, a third pair of arms 104c is applied to a portion of tissue on the first side of the tissue opening, proximal of the first pair of arms 104, and each subsequent pair of arms 104 being applied to a portion of tissue opposing the immediately prior pair of arms 104 in an alternating zipper-like manner. A distance between each of the pairs of arms 104 is selected such that applying the clip 102 to the tissue opening in this zipper-like fashion draws opposing edges of the tissue opening together to close the wound.

Each of the arms 104 is shaped such that, even when the arms 104 are in the closed configuration (i.e, the second ends 112 of the arms 104 are moved toward one another to grip tissue), a gap 120 exists between the opposing arms of each of the pair of arms 104 to accommodate a portion of the mandrel 106 therebetween. In the closed configuration, the gap 120 is sized to slidably receive a proximal portion of the mandrel 106 (i.e., a portion of the mandrel proximal of the enlarged distal end 114). Thus, when the enlarged distal end 114 of the mandrel 106 is received between the arms 104, the arms 104 are moved apart from one another, separating the second ends 112 from one another to permit tissue to be received therebetween. In one exemplary embodiment, the arms 104 may be curved along a length thereof such that the gap 120 formed therebetween is substantially circular.

Figure 2:
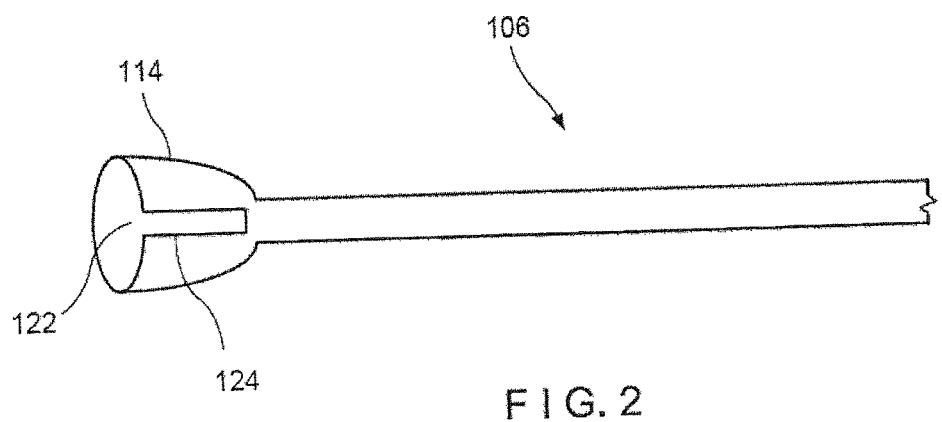
FIG. 2 shows a perspective view of a mandrel of the device of FIG. 1.

As shown in FIG. 2, the mandrel 106 extends along a longitudinal axis from a proximal end to the enlarged distal end 114 and includes a lumen 122 extending therethrough from the proximal end to the distal end 114. The mandrel 106 is received in the gap 120 between the arms 104 of the one or more pairs of arms 104 and is longitudinally movable relative to the clip 102 to move the arms 104 to the open configuration when the enlarged distal end 114 is received therebetween. Each pair of arms 104 reverts to the closed configuration under their natural bias when the enlarged distal end 114 is removed from therebetween. The proximal end of the mandrel 106 may be connected to a vacuum source to provide suction to the distal end 114 via the lumen 122. Thus, when the enlarged distal end 114 is received between a pair of arms 104 to move the arms 104 to the open configuration, a suction force applied to the distal end 114 draws tissue between the arms 104. In one exemplary embodiment, the mandrel 106 includes a longitudinal slot 124 extending longitudinally along a portion of a length of the enlarged distal end 114 to permit tissue to be drawn between the arms 104 even when the enlarged distal end is received therebetween. That is, when the mandrel 106 is positioned within the gap 120 with the longitudinal slot 124 facing the second ends 112 of the arms 104, the slot remains open to apply suction as the slot is not covered by the arms 104. Although the exemplary embodiment describes an enlarged distal end 114 including the longitudinal slot 124, it will be understood by those of skill in the art that the enlarged distal end 114 may include any of a variety of shapes, sizes and features so long as the distal end 114 permits tissue to be drawn between second ends 112 of the arms 104 while also being positioned therebetween.

As the mandrel 106 is drawn proximally relative to the clip 102, each pair of arms 104 is sequentially closed (from a distal-most one of the pair of arms 104 to a proximal-most one of the pair of arms 104) as the enlarged distal end 114 is withdrawn from between the pairs of arms 104. It will be understood by those of skill in the art that mandrel 106 may also be moved distally with respect to the longitudinal element 108 to, for example, reopen a pair of arms 104 after they have moved to the closed configuration. The enlarged distal end 114 may be positioned between adjacent clips 102 to permit all of the clips 102 to revert to their closed configurations.

The proximal end of the longitudinal element 108 may be connected to the proximal end of the control member via a frangible link designed to break when, for example, subject to a force exceeding a predetermined threshold level or when a bending moment is applied thereto. The longitudinal element 108 and the control member may be, for example, connected to one another via an adhesion or welding designed to break upon application of a predetermined force. In another example, the longitudinal element 108 and the control member may be integrally formed with a frangible link formed therein as a recess or cut-out reducing a cross-sectional area thereof. Thus, when all of the arms 104 of the clip 102 have been clipped over tissue, as desired, the control member may be drawn proximally, or bent relative to the longitudinal element 108, to separate the clip 102 from a proximal portion of the device 100 after which the rest of the device 100 may be withdrawn from the body or moved to a second location for deployment of another clip 102 (by repeating the same procedure).

According to an exemplary surgical technique using the device 100, the clip 102 is inserted to a target area within a body via, for example, a working channel of an endoscope inserted into a body lumen via a naturally occurring body orifice. Those skilled in the art will understand that the device 100 may be inserted through any other suitable access device and may enter the body via an incision or other opening. The exemplary surgical technique describes the usage of a clip 102 including more than one pair of arms 104. As described above, however, the clip 102 may comprise a single pair of arms 104. The clip 102 according to this exemplary method is inserted into the body in an insertion configuration in which the enlarged distal end 114 of the mandrel 106 is distal of the first (distal-most) pair of arms 104a. Once the clip 102 has reached the target area, the clip 102 is moved distally relative to the mandrel 106 to position the enlarged distal end 114 between a first pair of arms 104a moving the arms 104a to the open configuration, as shown in FIG. 3. A suction force is then applied through the mandrel 106 to draw a portion of tissue along a first side of a tissue opening between the second ends 112 of the arms 104a. As shown in FIG. 4, the mandrel 106 is then drawn proximally relative to the clip 102 to remove the enlarged distal end 114 from between the arms 104a permitting the arms 104a to revert under their bias to their closed configuration gripping the tissue therebetween. Once the first pair of arms 104a has been clipped over the desired portion of tissue, the clip 102 is moved toward a second side of the tissue opening opposite the first side to position the gripped portion of the first side toward the second side. The mandrel 106 is drawn farther proximally relative to the longitudinal element 108, as shown in FIG. 5, until the enlarged distal end 114 is received between the second pair of arms 104b moving the arms 104b to the open configuration. The suction force is then applied to draw tissue along the second side of the tissue opening between the second ends 112 of the arms 104b. Once the portion of tissue along the second side has been received between the second ends of the arms 104b, the mandrel 106 is moved proximally relative to the longitudinal element 108 permitting the arms 104b to close over the tissue received therebetween, thereby holding portions of the first and second sides of the tissue opening together. Where the clip 102 includes just two pairs of arms 104a, 104b, the clip 102 is then deployed in the body by, for example, drawing the control member, which is coupled to the proximal end of the longitudinal element 108 via the frangible link, proximally until the frangible link fails. Alternatively, a bending moment may be applied to the frangible link via the control member to break the frangible link separating the clip 102 from the device 100.

In a further embodiment in which the clip 102 includes more than two clips 102a, 102b, the mandrel 106 is moved further proximally relative to the clip 102 until the enlarged distal end 114 is received between the third pair of arms 104c moving the arms 104c to the open configuration. The clip 102 is again moved toward the first side of the tissue opening to draw a portion of tissue along the first side, proximal of the portion of tissue gripped by the first pair of arms 104a, between the second ends 112 of the arms 104c via the suction force through the mandrel 106. It will be understood by those of skill in the art that the above steps would be repeated for each of the subsequent pair of arms 104, each of which is applied over a portion of tissue on an opposing side of the tissue opening of the immediately distal pair of arms 104 such that the pairs of arms 104 of the clip 102 are applied alternatingly over a length of the tissue opening in a zipper-like fashion to close the tissue opening. Once all of arms 104 of the clip 102 have been applied about the tissue opening, the clip 102 is deployed, as described above.

Figure 6:
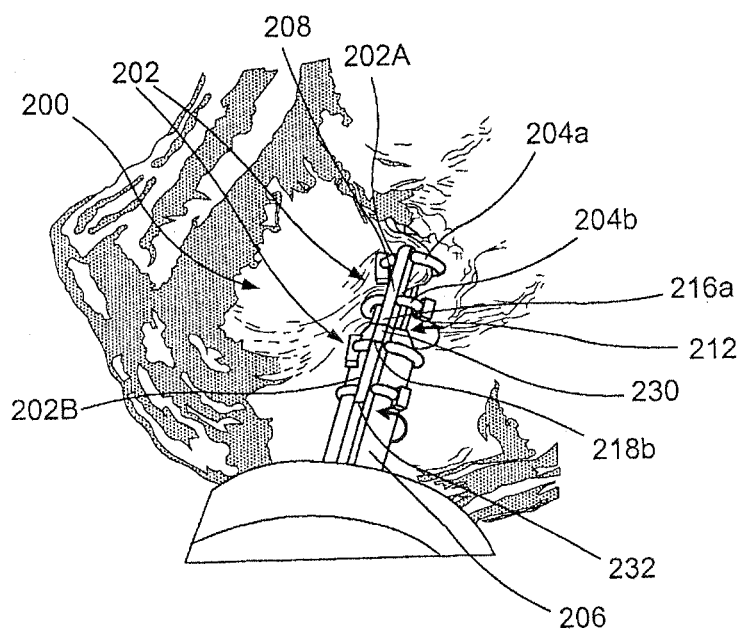
FIG. 6 shows a perspective view of a device according to a second exemplary embodiment of the present disclosure.
Figure 7:
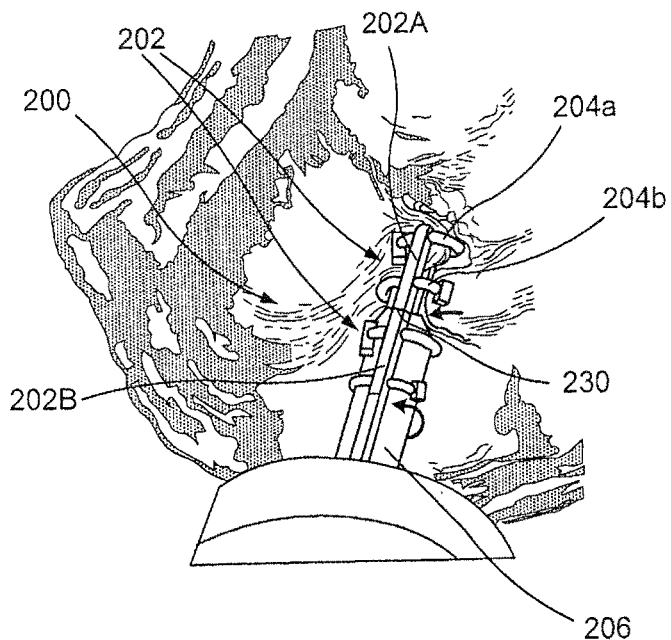
FIG. 7 shows another perspective view of the device of FIG. 6.
Figure 8:
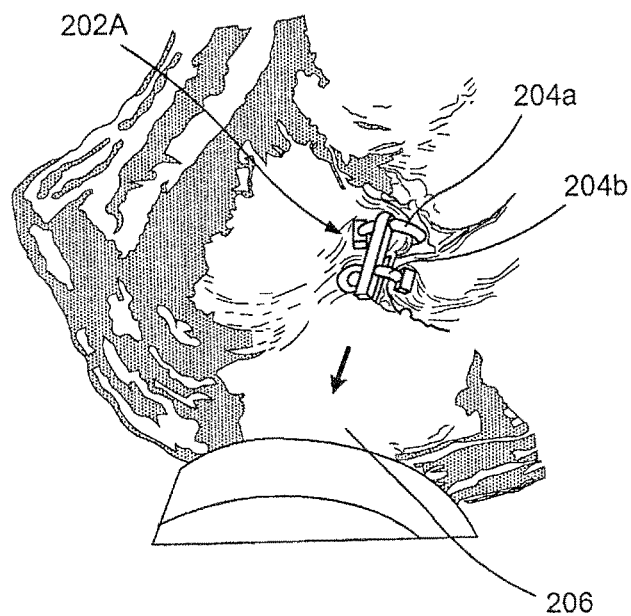
FIG. 8 shows a perspective view of a first clip member of the device of FIG. 6, deployed in a body.

As shown in FIGS. 6-8, a tissue closure device 200 according to a second exemplary embodiment of the present disclosure comprises a plurality of clips 202, each of which is substantially similar to the clip 102 described above. Although the exemplary embodiments show and describe two clips 202, it will be understood by those of skill in the art that the device 200 may include any number of clips 202. The clips 202 are separably coupled to one another so that multiple clips 202 may be applied over tissue to close one or more tissue openings, without having to insert and remove multiple devices for each clip applied. Similarly to the clip 102, the clip 202 includes one or more pair of arms 204 extending laterally from a longitudinal member 208 from a first end 210 to a second end 212. Each pair of arms 204 is separated from adjacent pairs of arms 204 along a length of the longitudinal element 208 and each of these pairs of arms 204 is movable between an open configuration in which second ends 212 are separated from one another to receive tissue and a closed configuration in which the second ends 212 are moved toward one another to grip tissue received therebetween. The arms 204 are biased toward the closed configuration so that when an enlarged distal end 214 of a mandrel 206, which is substantially similar to the mandrel 106, is received between the arms 204 of a given pair of arms 204, the arms 204 are separated from one another in the open configuration. The longitudinal elements 208 of the clips 202 are coupled to adjacent clips 202 via frangible links 230 such that longitudinal axes of the longitudinal elements 208 are coaxial with one another. For example, a proximal end 216a of a first one of the clips 202A may be coupled to a distal end 218b of a second one of the clips 202B. The frangible link 230 may be designed to break, for example, when subject to a force exceeding a predetermined threshold level or when subject to a bending moment as described above. Although the exemplary embodiment only shows two clips 202, it will be understood by those of skill in the art that the device 200 may include any number of clips 202 coupled to one another via the frangible link 230 between adjacent ones of the clips 202.

Similarly to the device 100, the tissue closure device 200 may further comprise a handle connected to the proximal end of the mandrel 206 and a proximal end of a control member (not shown), a distal end of which is connected to a proximal end of a longitudinal element 208 of a proximal-most one of the clips 202 via a frangible link 232 such that when the clips 202 are inserted into target area within a body, the handle extends proximally therefrom to be accessible by a user of the device 200. The handle may include an actuator for moving the mandrel 206 and the clips 202 relative to one another to move individual pairs of arms 204 of the clips 202 between the open and closed configuration.

The device 200 may be used to provide tissue closure in substantially the same way as the device 100. The following exemplary surgical method describes the application of a first and second clip 202A, 202B, each including two pairs of arms 204a, 204b. It will be understood by those of skill in the art, however, that the device 200 may include any number of clips 202, each of which include one or more pairs of arms 204. In particular, the clips 202 may be inserted into the body in an insertion configuration in which enlarged distal end 214 of mandrel 206 is distal of the first (distal-most) pair of clip arms 204a of the first clip 202A. Once a distal end of the device 200 is adjacent the target tissue, the first clip 202A, and consequently all of the subsequent clips 202 connected thereto, are moved distally with respect to the mandrel 206 so that the enlarged distal end 214 is received the first pair or arms 204a to move the clip arms 204a from the biased closed configuration to the open configuration. A suction is applied through the mandrel 206 to draw tissue along a first side of a tissue opening between the second ends 212 of the first arms 204a. The mandrel 206 is then moved proximally with respect to the clips 202 so that the enlarged distal end 214 is moved out from between the arms 204a so that arms 204a is permitted to revert to the biased closed configuration and grip the tissue received therebetween, as shown in FIG. 6. The mandrel 206 is moved proximally until the enlarged distal end 214 is received between second pair of arms 204a of the first clip 202A. The clip 202A is then moved toward a second side of the tissue opening opposite the first side such that a portion of tissue therealong may be drawn between the second ends 212 of the second pair of arms 204b, closing a portion of the tissue opening. Once the target tissue is received therebetween, the mandrel 206 is drawn farther proximally with respect to the second pair of arms 204b so that the enlarged distal 214 is no longer received between the arms 204b, permitting the arms 204b to revert to the biased closed configuration to grip the tissue received therebetween, as shown in FIG. 7. Upon clipping of the first and second sides of the tissue opening via the arms 204a, 204b, the first clip 202A is deployed within the body, as shown in FIG. 8, by applying a predetermined threshold force to the frangible link 230 to break the link 230 and separate the first clip 202A from a second one of the clips 202B. The second clip 202B may be applied to a portion of the tissue opening proximal of the first clip 202A or to another tissue opening within the body in substantially the same way as described above. Subsequent clips 202 may be similarly applied and deployed in the body.

Figure 9:
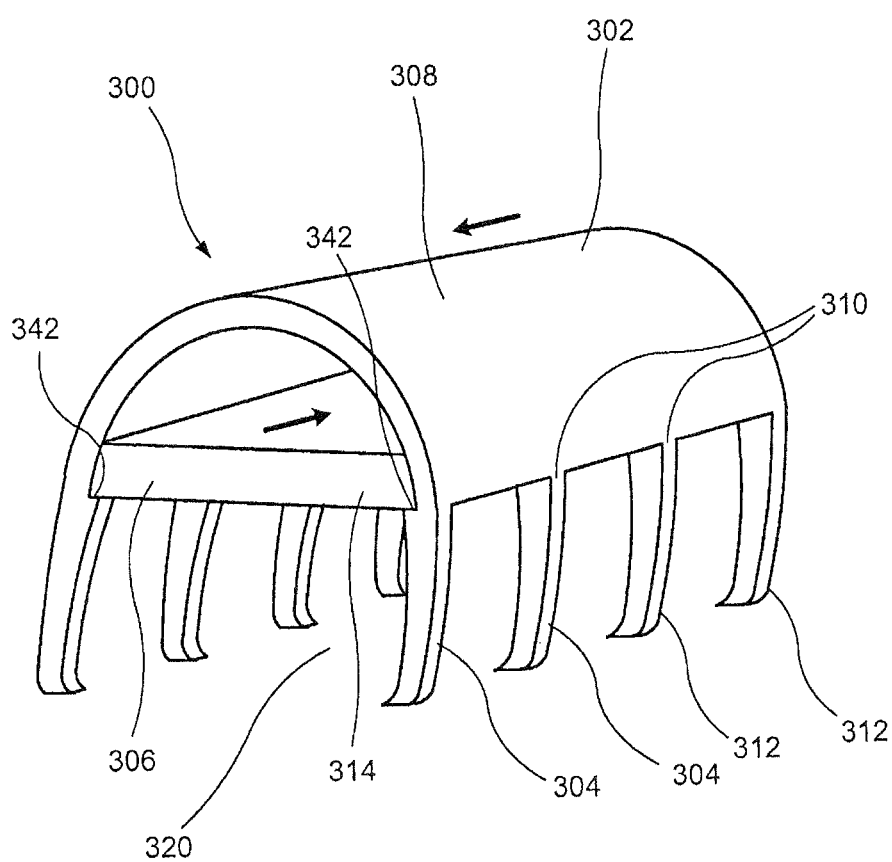
FIG. 9 shows a perspective view of a device according to a third exemplary embodiment of the present disclosure.
Figure 10:
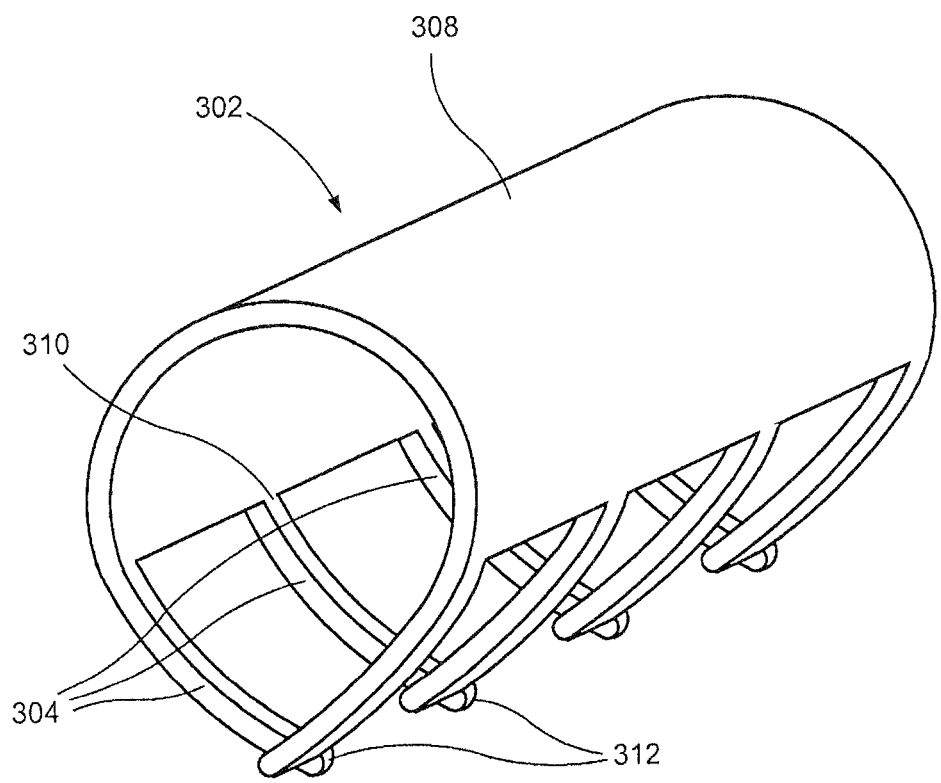
FIG. 10 shows a perspective view of a clip according to the device of FIG. 9.
Figure 11:
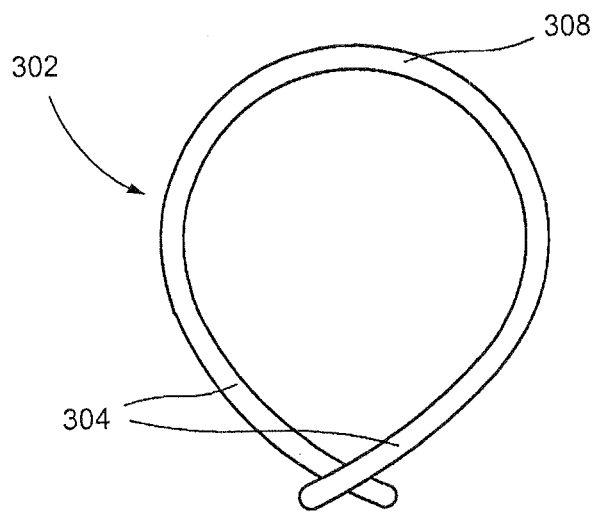
FIG. 11 shows a lateral cross-sectional view of the clip of FIG. 10.

As shown in FIGS. 9-11, a device 300 may be substantially similar to the device 100 described above, comprising a clip 302 including one or more pair of arms 304 and a pin 306 for moving the clip 302 between an open tissue-receiving configuration and a closed tissue-gripping configuration. Similarly to the clip 102, the arms 304 are formed in pairs extending laterally (in opposite directions from one another) from a longitudinal element 308. Each of the arms 304 extends from a first end 310 attached to the longitudinal element 308 to a second end 312 with the pin 306 longitudinally movable relative to the longitudinal element 308 to move the arms 304 between the open and closed configurations. As shown in FIGS. 10 and 11, the arms 304 are biased toward the closed configuration in which the second ends 312 of the arms 304 are drawn toward one another to grip tissue received therebetween but are held in the open configuration by the pin 306 as long as it is received between the arms 304. The clip 302 may be formed by, for example, laser cutting nitinol tubing such that the arms 304 are integrally formed with the longitudinal member 308 and the longitudinal member 308 is formed via a portion of the tubing so that the longitudinal element 308 is curved about a longitudinal axis thereof. The clip 302 may include a shoulder 342 extending along a length of an inner surface of the longitudinal element 308 on opposing sides thereof, the shoulder 342 sized and shaped to slidably receive the pin 306 therebetween.

The pin 306, which in this embodiment is substantially planar, extends longitudinally from a proximal end (not shown) to a distal end 314 and is sized and shaped so that, when slidably received between opposing arms 304 of each pair of the arms 304 and seated in the shoulder 342, the arms 304 are maintained in the open configuration with the second ends 312 of the opposing arms 304 of each pair separated from one another to receive tissue therebetween. It will be understood by those of skill in the art that the planar shape of the pin 306 holds the clip 302 in the open configuration without interfering with the functioning of the arms 304. In other words, the pin 306 is received between the first ends 310 of the arms 304 and does not extend into a space 320 between opposing arms of the pair of arms 304 in which tissue would be received.

An exemplary surgical technique using the device 300 is substantially similar to the technique described above in regard to the device 100. Similarly to the device 100, the clip 302 is inserted into the body, for example, via a working channel of an endoscope or other insertion device. The clip 302, however, is inserted into the body in the open configuration—i.e., with the pin 306 received between the arms 304. The clip 302 is positioned with opposing arms 304 of the pairs positioned adjacent opposing sides of a tissue opening. When the arms 304 have been positioned over a target portion of tissue as desired, the pin 306 is withdrawn proximally relative to the clip 302 so that, as it is removed from between the arms 304, the clip 302 moves to the closed configuration to grip the target tissue. Since opposing ones of each pair of arms 304 are positioned adjacent to opposing sides of the tissue opening, as the clip 302 moves to the closed configuration, the arms 304 draw edges of the tissue opening toward one another to close the tissue opening.

As shown in FIGS. 12-13, a device 400 according to another embodiment of the present disclosure is substantially similar to the device 300 described above, comprising a clip 402 including one or more pair of arms 304 movable between an open tissue-receiving configuration and a closed tissue-gripping configuration. The clip 402 is substantially similar to the clip 302 described above, with the arms 404 extending in pairs laterally from a longitudinal element 408. Each of the arms 404 extends in a direction opposite that of an second arm of its pair from a first end 410 attached to the longitudinal element 408 to a second end 412. Rather than a pin, however, the device 400 comprises an inflatable balloon 406 which, when inflated, maintains the clip 402 the open configuration. In particular, the balloon 406 is positioned within the clip 402 along an inner surface 444 of the longitudinal element 408. The device 400 is inserted to a target site in a body in the closed configuration—i.e., with the balloon 406 deflated so that the second ends 412 of opposing arms 404 of each pair are drawn together under the natural bias of the clip 402 in a gripping configuration. Once the clip 402 is positioned adjacent to a target site as desired, the balloon 406 is inflated to move the opposing arms 404 away from one another into the open configuration. As shown in FIG. 13, the clip 402 and the balloon 406 are correspondingly sized and shaped so that, when the balloon 406 is in the inflated state, the balloon 406 does not interfere with the functioning of the arms 404—i.e., the inflated balloon 4060 does not enter a space 420 between opposing ones of the pair of arms 404 in which tissue would be received. Once the clip 402 has been positioned as desired with opposing arms of each of the pairs of arms 404 adjacent portions of tissue on opposing sides of a tissue opening, the balloon 406 is again deflated to permit the clip 402 to revert to the closed configuration closing the tissue opening. It will be understood by those of skill in the art, that once the clip 402 has gripped tissue, as desired, the inflatable balloon 406 may be removed therefrom.

It will be apparent to those skilled in the art that various modifications and variations may be made in the structure and the methodology of the present disclosure, without departing from the spirit or scope of the disclosure. Thus, it is intended that the present disclosure cover modifications and variations of the disclosure provided that they come within the scope of the appended claims and their equivalents.

What is claimed is:

1. A tissue closure device, comprising:
a first clip including a first longitudinal element extending along a longitudinal axis from a proximal end to a distal end and a first pair of arms extending laterally from the first longitudinal element, the first pair of arms being movable between an open configuration in which free ends of the first pair of arms are separated from one another to receive a target tissue therebetween and a closed configuration in which the free ends of the first pair of arms extend toward one another to grip the target tissue therebetween, the first pair of arms being biased toward the closed configuration; and
a sliding element extending from a proximal end to a distal end and movable along the longitudinal axis relative to the first clip so that when a portion of the sliding element is received between the first pair of arms, the first pair of arms is moved from the biased closed configuration to the open configuration, wherein the sliding element comprises a lumen extending longitudinally therethrough from the proximal end to the distal end, and
a vacuum source coupled to a proximal end of the sliding element to provide a suction force to the distal end via the lumen,
wherein the first clip includes a second pair of arms extending laterally from the first longitudinal element, the second pair of arms movable between an open configuration in which free ends of the second pair of arms are separated from one another to receive a target tissue therebetween and a closed configuration in which the free ends of the second pair of arms extend toward one another to grip the target tissue therebetween, the second pair of arms being biased in the closed configuration and positioned along the first longitudinal element proximally of the first pair of arms.

2. The device of claim 1, wherein the sliding element is a mandrel including an enlarged distal end and the lumen extends longitudinally through the mandrel, a portion of the mandrel extending proximally from the enlarged distal end sized and shaped to be slidably received within a gap formed between the first pair of arms in the closed configuration, the mandrel being longitudinally movable relative to the first clip so that when the enlarged distal end is received between the first pair arms of the first clip, the first clip is moved from the biased closed configuration to the open configuration.

3. The device of claim 2, wherein the mandrel includes a longitudinal slot extending along a length of the enlarged distal end so that, when the enlarged distal end is received between the first pair of arms, the longitudinal slot is aligned with a space between the free ends of the first pair of arms such that the tissue is receivable therebetween.

4. The device of claim 1, wherein the first pair of arms is formed via a flexible member passed through an opening extending laterally through the first longitudinal element.

5. The device of claim 1, further comprising a second clip including a second longitudinal element extending along a longitudinal axis from a proximal end to a distal end and a third pair of arms extending laterally from the second longitudinal element, the third pair of arms movable between an open configuration in which free ends of the third pair of arms are separated from one another to receive a target tissue therebetween and a closed configuration in which the free ends of the third pair of arms extend toward one another to grip the target tissue therebetween, the third pair of arms biased in the closed configuration.

6. The device of claim 5, wherein the second clip includes a fourth pair of arms extending laterally from the second longitudinal element, the fourth pair of arms movable between an open configuration in which free ends of the fourth pair of arms are separated from one another to receive a target tissue therebetween and a closed configuration in which the free ends of the fourth pair of arms extend toward one another to grip the target tissue therebetween, the fourth pair of arms being biased in the closed configuration and positioned along the second longitudinal element proximally of the third pair of arms.

7. The device of claim 5, wherein the proximal end of the first longitudinal element of the first clip is connected to the distal end of the second longitudinal element of the second clip via a frangible link.

8. The device of claim 1, wherein each arm of the first pair of arms extend from a first end connected to the first longitudinal element to a second free end.

9. The device of claim 1, wherein the first pair of arms are integrally formed with the first longitudinal element.

10. A tissue closure device, comprising:
a first clip including a first longitudinal element extending along a longitudinal axis from a proximal end to a distal end and a first pair of arms extending laterally from the first longitudinal element, the first pair of arms being movable between an open configuration in which free ends of the first pair of arms are separated from one another to receive a target tissue therebetween and a closed configuration in which the free ends of the first pair of arms extend toward one another to grip the target tissue therebetween, the first pair of arms being biased toward the closed configuration;

a second clip including a second longitudinal element extending along a longitudinal axis from a proximal end to a distal end and a second pair of arms extending laterally from the second longitudinal element, the second pair of arms movable between an open configuration in which free ends of the second pair of arms are separated from one another to receive a target tissue therebetween and a closed configuration in which the free ends of the second pair of arms extend toward one another to grip the target tissue therebetween, the second pair of arms biased in the closed configuration;

a sliding element extending from a proximal end to a distal end and movable along the longitudinal axis relative to the first clip so that when a portion of the sliding element is received between the first pair of arms, the first pair of arms is moved from the biased closed configuration to the open configuration, wherein the sliding element comprises a lumen extending longitudinally therethrough from the proximal end to the distal end, and a vacuum source coupled to a proximal end of the sliding element to provide a suction force to the distal end via the lumen.

11. The device of claim 10, wherein the sliding element is a mandrel including an enlarged distal end and the lumen extends longitudinally through the mandrel, a portion of the mandrel extending proximally from the enlarged distal end sized and shaped to be slidably received within a gap formed between the first pair of arms in the closed configuration, the mandrel being longitudinally movable relative to the first clip so that when the enlarged distal end is received between the first pair arms of the first clip, the first clip is moved from the biased closed configuration to the open configuration.

12. The device of claim 10, wherein the first pair of arms is formed via a flexible member passed through an opening extending laterally through the first longitudinal element.

13. The device of claim 10, wherein the second clip includes a third pair of arms extending laterally from the second longitudinal element, the third pair of arms movable between an open configuration in which free ends of the third pair of arms are separated from one another to receive a target tissue therebetween and a closed configuration in which the free ends of the third pair of arms extend toward one another to grip the target tissue therebetween, the third pair of arms being biased in the closed configuration and positioned along the second longitudinal element proximally of the second pair of arms.

14. The device of claim 10, wherein the proximal end of the first longitudinal element of the first clip is connected to the distal end of the second longitudinal element of the second clip via a frangible link.

15. The device of claim 11, wherein the mandrel includes a longitudinal slot extending along a length of the enlarged distal end so that, when the enlarged distal end is received between the first pair of arms, the longitudinal slot is aligned with a space between the free ends of the first pair of arms such that the tissue is receivable therebetween.

16. The device of claim 10, wherein each arm of the first pair of arms extend from a first end connected to the first longitudinal element to a second free end.

17. The device of claim 16, wherein the sliding element is a planar pin slidably receivable between first ends of the first pair of arms.

18. The device of claim 10, wherein the first pair of arms are integrally formed with the first longitudinal element.

* * * * *